United States Patent [19]

Sachse

[11] Patent Number: 5,295,954
[45] Date of Patent: Mar. 22, 1994

[54] ARRANGEMENT CONSISTING OF URETER TUBE, (STENT) MANDRIN AND AUXILIARY TUBE

[76] Inventor: Hans-Ernst Sachse, Lerchenstr. 55, 8500 Nürnberg 90, Fed. Rep. of Germany

[21] Appl. No.: 758,044

[22] Filed: Sep. 12, 1991

[30] Foreign Application Priority Data

Nov. 20, 1990 [DE] Germany ............... 9015815

[51] Int. Cl.⁵ .............................................. A61M 25/00
[52] U.S. Cl. ........................................ 604/8; 604/170; 604/281
[58] Field of Search ............... 604/264, 280, 281, 283, 604/164, 165, 170, 8; 128/656–658

[56] References Cited

U.S. PATENT DOCUMENTS

| | | | |
|---|---|---|---|
| 4,610,657 | 9/1986 | Densow | 604/8 |
| 4,713,049 | 12/1987 | Carter | 604/8 |
| 4,713,058 | 12/1987 | Sachse | 604/170 |
| 4,738,667 | 4/1988 | Galloway | 604/281 |
| 4,787,884 | 11/1988 | Goldberg | 604/8 |
| 4,798,591 | 1/1989 | Okada | 604/281 |
| 4,820,262 | 4/1989 | Finney | 604/8 |
| 4,834,702 | 5/1989 | Rocco | 604/170 |
| 4,874,360 | 10/1989 | Goldberg et al. | 604/8 |
| 4,944,729 | 7/1990 | Buckberg et al. | 604/264 |
| 4,957,479 | 9/1990 | Roemer | 604/8 |
| 4,973,301 | 11/1990 | Nissenkorn | 604/8 |
| 4,986,814 | 1/1991 | Burney et al. | 604/264 |
| 4,990,133 | 2/1991 | Solazzo | 604/8 |
| 5,052,998 | 10/1991 | Zimmon | 604/8 |
| 5,074,849 | 12/1991 | Sachse | 604/280 |
| 5,116,309 | 5/1992 | Coll | 604/8 |

FOREIGN PATENT DOCUMENTS 286756 10/1988 European Pat. Off. ............ 604/280

*Primary Examiner*—Ralph Lewis
*Attorney, Agent, or Firm*—Keil & Weinkauf

[57] ABSTRACT

An arrangement comprising a ureter tube, a mandrin having an outer shaft and an inner shaft, the inner shaft being longitudinally movable relatively to the outer shaft, and an auxiliary tube, the ureter tube and auxiliary tube being slidable onto the mandrin, and the mandrin and the ureter tube being releasably connected with each other; pear the proximal end of the mandrin outer shaft provisions are made for facilitating the introduction of an X-ray contrasting medium, and the distal end of the ureter tube having at its face a central opening, whereby the contrasting medium is enabled to flow through the length of the mandrin outer shaft in a substantially rectilinear path and to then exit the arrangement at the central opening. Focusing on another aspect of the arrangement, the distal end of the mandrin outer shaft and the mandrin inner shaft are approximately flush with the outer surface of the ureter tube tip surrounding the central opening, whereby traumatization of the ureter during introduction of the ureter tube with the mandrin inner shaft and the mandrin outer shaft therein is avoided.

14 Claims, 5 Drawing Sheets

ARRANGEMENT CONSISTING OF URETER TUBE, (STENT) MANDRIN AND AUXILIARY TUBE

BACKGROUND OF THE INVENTION AND PRIOR ART

The invention relates to an arrangement comprising a ureter tube, (ureter stant), a mandrin having an outer shaft and an inner shaft which latter is longitudinally movable relatively to the outer shaft, and an auxiliary tube, the ureter tube and auxiliary tube being slidable onto the mandrin, and the mandrin and the ureter tube being releasably connected with each other. Such art arrangement is the subject matter of German Laid-open Application DE-OS 38 24 244, corresponding to my U.S. patent application Ser. No. 468,017, filed Jan. 22, 1990 now U.S. Pat. No. 5,074,849 or the earlier German Patent Application P 39 00 738.3, corresponding to my U.S. patent application Ser. No. 462,221, filed Jan. 9, 1990 now abandoned. In this arrangement ureter tube, mandrin and auxiliary tube form a functional unit which, in order to improve introduction, makes possible forward as well as rearward movements or rotational movements of the ureter tube and also curving of the ureter tube tip and, upon proper placement of the ureter tube permits ready removal of the mandrin and the auxiliary tube without problems. Furthermore, as to the prior art mention should be made of DE-OS 38 24 244. This Laid-open Application provides a releasable screw connection between mandrin and ureter tube (called "drainage tube" in this earlier publication). Such a screw connection may take place between an outer thread of the mandrin tip and a cooperating thread in the tip range of the interior of the ureter tube. In another embodiment of DE-OS 38 24 244 provisions are made so that the ureter tube, in the range of its tube end adjoining the auxiliary tube, has an inner thread which is engaged by an outer thread of the mandrin. In both of the above instances the thread of the ureter tube can either be directly provided in its material or in a little tube which is firmly connected with the ureter tube. Moreover, it is possible in these embodiments that the end of the ureter tube near the end of the auxiliary tube is guarded against rotational movement with respect to the auxiliary tube tip by means of projections and recesses engaging the latter. In this manner, in the process of establishing or releasing the screw connection between mandrin and ureter tube longitudinal displacements or rotational movements between ureter tube and auxiliary tube are prevented. Finally, DE-OS 38 24 244 provides as a further solution that the auxiliary-tube-adjoining end of the ureter tube has one or more obliquely extending recesses, and that the auxiliary tube has one or more obliquely extending projections which are somewhat smaller than the recesses and may be engaged with each other as a rotation preventing means. The mandrin tip in this instance has a section with an angular cross-sectional profile which extends into a correspondingly formed lumen of the auxiliary-tube-adjoining end of the ureter tube and thus prevents undesired rotational movements of the mandrin within the ureter tube. Auxiliary tube and mandrin can be firmly connected in the end range, this connection, however, being releasable if required.

The invention described below may be used with arrangements according to DE-OS 39 00 738 as well as with arrangements according to DE-OS 38 24 244 and particularly also with arrangements which exhibit features of DE-OS 39 00 738 and of DE-OS 38 24 244.

To be sure in the embodiment according to FIG. 1 of DE-OS 39 00 738 it was possible, as a matter of principle, to inject upon withdrawal of the mandrin inner shaft through the mandrin outer shaft and by way of drainage canals located above the end of the mandrin outer shaft, an X-ray contrasting medium into the urethra and thus further into the renal pelvis outlet system. However, this was possible only incompletely since on the one hand the flow direction of the X-ray contrast medium had to change twice by 90° in the process, and since particularly the X-ray contrasting medium had to find its way through the relatively narrow gap between ureter tube and ureter.

OBJECT AND SUMMARY OF THE INVENTION

By way of contrast, it is the object or problem of the invention, starting from the arrangement of the kind set forth at the outset which is based on the earlier applied subject matter of FIG. 1 of DE-OS 39 00 738, to insure that an X-ray contrasting medium can safely be introduced, in a sufficient amount and with a corresponding pressure, into the urethra and into the renal pelvis outlet system, by way of the inserted ureter tube.

The solution of this problem is primarily seen in that near the distal end of the mandrin outer shaft there are provided means for facilitating the introduction of an X-ray contrasting medium, and that the proximal end of the ureter tube has at its face a central opening, whereby the contrasting medium is enabled to flow through the length of the mandrin outer shaft in a substantially rectilinear path and to then exit the arrangement at the central opening.

The invention thus makes it possible, upon withdrawal of the mandrin inner shaft, to inject the X-ray contrasting medium by way of the mandrin outer shaft into the urethra in almost rectilinear continuation of the longitudinal axis of ureter tube and mandrin outer shaft, whereby the X-ray contrasting medium then reaches the renal pelvis outlet system by way of the upper or distal end of the urethra. "Upper end of the ureter tube" is meant to denote the end which is introduced into the urethra. Thus the previously conventional insertion of special ureter catheters into the urethra for the purpose of introduction of the X-ray contrasting medium, and thereafter the separate placement of the ureter tube are no longer necessary. Rather, only one of these procedural steps, namely the placement of the ureter tube, namely into the lower end of the urethra, needs now to take place. Thereafter upon withdrawal of the mandrin inner shaft, the X-ray contrasting medium can first be introduced in the described manner. Following this, the mandrin inner shaft is reinserted in order to stabilize the ureter tube and to insure the controllability of the ureter tube tip and the entire arrangement including the ureter tube already present in the urethra is advanced upwardly until the upper range of the ureter tube is located within the renal pelvis outlet system, while its lower range is still within the urinary bladder. Subsequently, mandrin and auxiliary tube are withdrawn in the usual manner whereby the flexible ends ("pig-tail") of the ureter tube secure it against an undesired displacement. Thus, according to the invention the surgeon is spared time and the patient is spared a repeated ureter-outlet locating procedure. In this manner, expenses are saved due to the now reduced operating time and the reduced usage of catheter material. For the sake of completeness it may be mentioned that open-ended ureter tubes are known per se namely in order to make it possible to move a ureter tube on a guiding wire, either from the direction of the kidney in the direction of the bladder, vice versa. However, this has no connection with the invention and the solution afforded thereby of the above-mentioned problem.

As a matter of principle, the introducing of the X-ray contrasting medium according to the invention can be materialized even if upon insertion of the ureter tube the mandrin is not flush with the outer surface of the ureter tube surrounding the ureter tube tip; or if upon withdrawal of the mandrin inner shaft the mandrin outer shaft still protrudes somewhat from the ureter tube tip or if it terminates below the opening of the ureter tube tip. However, in order to avoid traumatizations of the urethra during the introduction of the ureter tube into the lower end of the urethra the arrangement just mentioned is advisable, that is that mandrin inner shaft and mandrin outer shaft are at least approximately flush with the outer surface of this opening or with the corresponding end of the ureter tube.

A subsidiary feature resides in that the front face of the tip of the mandrin inner shaft is domed outwardly and, when positioned approximately flush with the opening of the ureter tube tip, continues the outwardly directed curvature of the ureter tube tip. It is considered to be within the confines of the foregoing other aspect of the invention that the mandrin inner shaft or both the mandrin inner shaft and the mandrin outer shaft outwardly protrude somewhat beyond the ureter tube tip. This protrusion may have only a minor extent, for example 1 mm. However in special cases this extent may also be in the order of, say, 15 mm. If obstructions, especially stones are present in the urethra, the mandrin which is considerably thinner than the ureter tube may squeeze itself between stone and urethra wall and may thus urge the stone to the side whereby room is provided for the introduction of the tip of the ureter tube.

According to another feature of the ureter tube includes drainage channels merely in the proximal or tip range and the distal range; the mandrin over shaft terminates somewhat upwardly of the clamping connection between the last-mentioned shaft and the ureter tube; and a screw clamp is provided centrally with respect to the mandrin and the auxiliary tube, this screw clamp serving to releasably connect the auxiliary tube and the mandrin outer shaft. This feature makes it possible that the X-ray contrasting medium can flow through the lumen of the ureter tube to the central lumen at its tip and thence further outwardly. This is advantageous particularly if a ureter tube of relatively small inner diameter is used so that when the mandrin outer shaft is advanced toward the tip of the ureter tube the cross-sectional flow through the passage or the X-ray contrasting medium would be very small, that is equal to the then remaining relatively small inner diameter of the mandrin outer shaft. However then, according to the last-mentioned feature, the inner diameter of the ureter tube is available as the lumen.

A further feature relates to a releasable screw connection between mandrin an ureter tube whereby rotational movement between ureter tube and auxiliary tube is prevented. Such screw connections are known per se through the initially acknowledged DE-OS 38 24 244.

BRIEF DESCRIPTION OF THE DRAWING

Further advantages and features of the invention will be evident from the following description, and the associated drawing of embodiments of the invention.

DETAILED DESCRIPTION OF THE PREFERRED EMBODIMENTS

Figure 1:
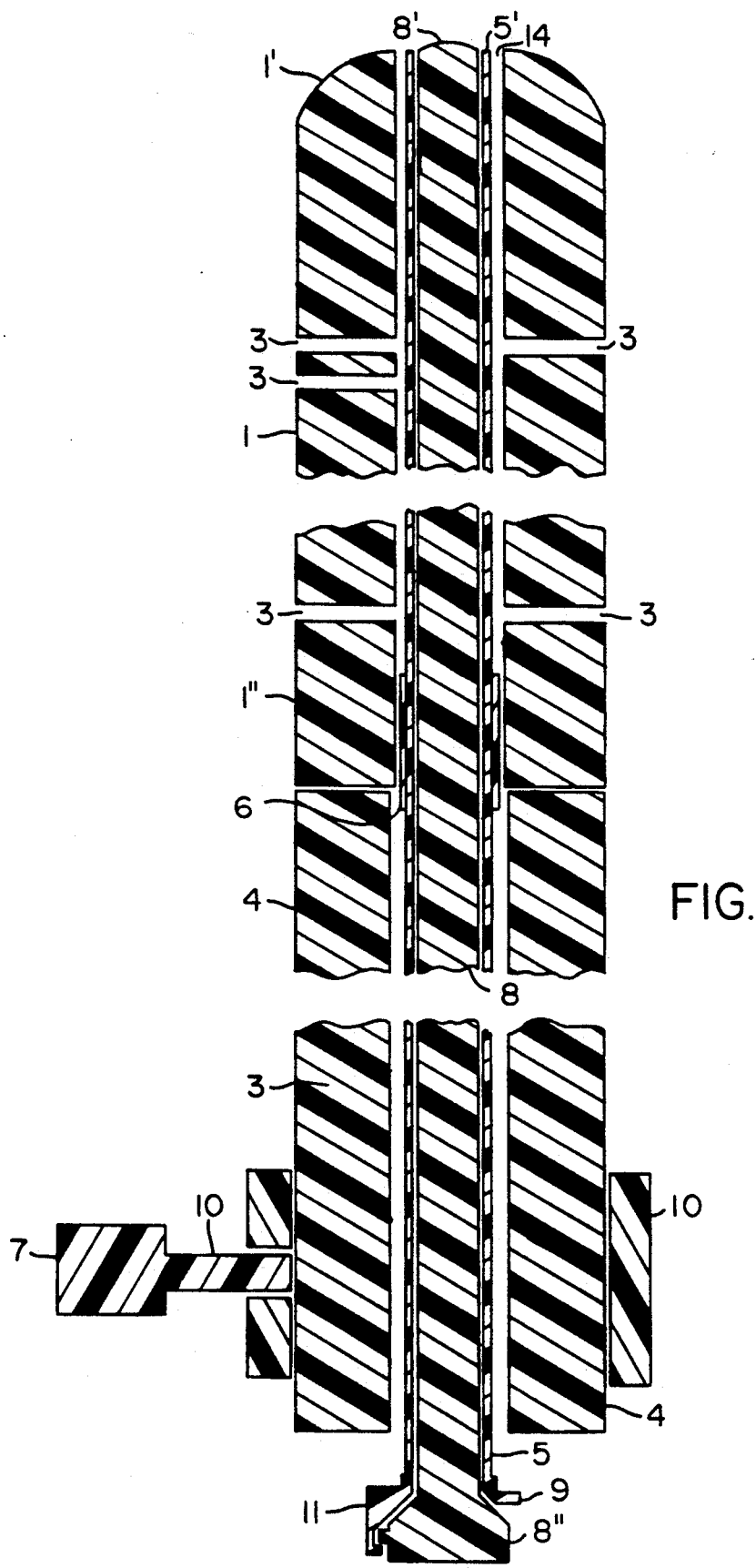
FIG. 1 is a first embodiment, shown in longitudinal section, of an arrangement according to the invention.

FIG. 1 of the drawings shows an arrangement with a ureter tube I which in the range of its tip shown in the upper part of FIG. 1 and in the range of its lower end as shown in FIG. 1 has an inherent curvature, that is a so-called "pig-tail tube" or "double-J tube". The ureter tube can, if desired, have different lengths with correspondingly chosen diameter and wall thickness. It can also have drainage channels. The ureter tube is made from an elastic plastic material which due to its inherent elasticity forms the aforementioned inherent curvatures of both ends of the ureter tube. In order that in the introduction of the ureter tube into the urethra the above-mentioned curvature of tip 1' and of end 1" of the ureter tube is eliminated, the relatively stiffer mandrin is inserted which imparts to the ureter tube overall a stretched form. This is known per se and besides is described in the two patent applications which have been pointed out above as prior art and prior patent right, respectively.

Figure 2:
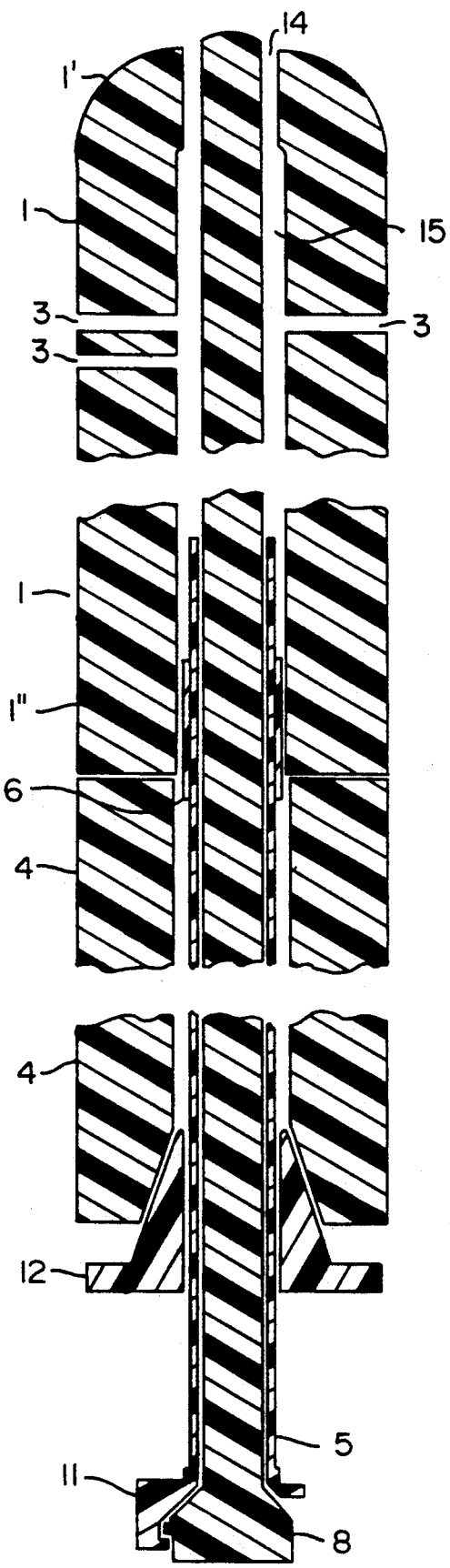
FIG. 2 is a second embodiment of the invention also shown in longitudinal section.

In the case of the invention the mandrin is a so-called double mandrin, that is it consists of a mandrin outer shaft 5 and a mandrin inner shaft 8. Between mandrin outer shaft 5 and the interior of the ureter tube 1 there is produced by means of a wall enlargement a clamping engagement through which all movements of the mandrin outer shaft are uniformly carried out by the ureter tube. This clamping engagement also brings about that during the introduction of the ureter tube or the movement within the urethra, mandrin and ureter tube are not undesirably displaced with respect to one another or are released from each other. Only in the later removal of the mandrin can the mandrin outer shaft 5 be withdrawn from the ureter tube 1 namely by overcoming the frictional force between enlargement on the one hand and the countersurface adjoining it on the other hand. The above-mentioned material enlargement and the clamping engagement between mandrin and ureter tube resulting therefrom can be attained in different ways, namely: in outwardly directed enlargement of the mandrin outer shaft; or an inwardly directed enlargement of the ureter tube; or an insert between mandrin outer shaft and ureter tube, which insert may also be inflatable. The aforementioned enlargement or inserts may extend up to the range between the outer mandrin shaft and inner auxiliary tube 4 which is also slid over the mandrin outer shaft and which with its upper end bears against the lower end of the ureter tube. During the withdrawal of the mandrin outer shaft from the ureter tube, the support of the auxiliary tube prevents that the friction between the enlargement 6 and the interior of the ureter tube takes the latter along in the pulling direction of the mandrin outer shaft, and withdraws this tube. With the aid of this auxiliary tube 4, the proper placement of the ureter tube is brought about, which auxiliary tube is firmly connected, for the introduction process, with the mandrin outer shaft 5 either by means of a clamp 10 (FIG. 1) or a screw connection 12 (FIG. 2).

FIG. 1 shows that in the upper tip 1' of the ureter tube there is provided a central opening 14 in which the mandrin terminates. According to this embodiment the upper end 8' of the mandrin inner shaft and the upper end of the mandrin outer shaft are inserted up to the tip 1' of the ureter tube and are approximately flush with the latter. The curvature of the outer surface of the ureter tube tip 1' approximately continues the curvature of tip 8' of the mandrin inner shaft so that overall an outwardly domed surface of the arrangement to be introduced into the urethra results which does not traumatize the urethra. If desired, mandrin inner shaft and outer shaft may protrude upwardly somewhat beyond the rim of the above-mentioned opening 14 of the ureter tube tip, for example by 1 mm. In special cases the mandrin may protrude from the tip further, for example by 10 mm (not shown in the drawing). In the representation according to FIG. 1 in which mandrin inner shaft 8 and outer mandrin shaft 5 are placed and held in the proper position with respect to each other, the ureter tube is introduced into the ureter. As soon as the ureter tube has reached the lower ureter section, the coupling 11 is released and the mandrin inner shaft withdrawn downwardly. Then the X-ray contrasting medium can be injected into the ureter, whereby it reaches the renal pelvis outlet system. In this manner the interior of the ureter and the renal pelvis outlet system are representable by X-rays, and this is required particularly for the further introduction of the ureter tube. For the introduction of the X-ray contrasting medium the mandrin outer shaft may be provided with a syringe-connecting stud 9 for the injection syringe. After the X-ray contrasting medium has been introduced the mandrin inner shaft 8 is reinserted and connected with the outer shaft by means of coupling 11. Subsequently, the unit consisting of mandrin, ureter tube and auxiliary tube is imparted the desired placement whereby the upper end 1' of the ureter tube comes to lie in the renal pelvis outlet system and the lower end 1" in the urinary bladder. Thereafter upon release of coupling 11 and of a clamping 10 of the mandrin with the auxiliary tube 4, the mandrin is withdrawn from the ureter tube whereby the auxiliary tube is urged from below against the ureter tube. Upon the removal of the mandrin the auxiliary tube can also be pulled out.

In the ureter tube 1 there may also be provided drainage channels 3. Upon removal of the entire mandrin, that is also the mandrin outer shaft 5, the ureter tube in the urethra may serve as a drainage tube by means of the apertures 3 and, of course, also by means of its inner lumen which is open at the upper as well as the lower end.

Figure 1A:
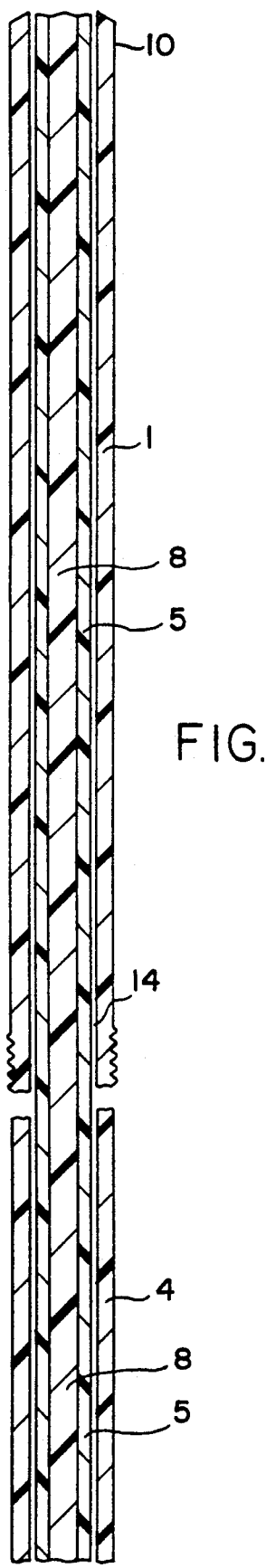
FIG. 1A shows a longitudinal cross-sectional view showing the auxiliary tube, the inner mandrin, the outer mandrin and the ureter tube ready for insertion into the ureter.

FIG. 1A shows the apparatus prior to insertion into the ureter. The ureter tube 1 contains in its lumen the outer mandrin 5 which contains in its lumen the inner mandrin 8. Ureter tube 1 and auxiliary tube 4 are thus over the mandrins 5, 8. The stiff mandrins, 5, 8 straighten the two memory parts at the two ends of the ureter tube.

The proximal end of the ureter tube 1 is releasably clamped 7 with the outer mandrin 5. Without clamping 7, the auxiliary tube 4 is easily slidably over the outer mandrin 5 and can push or keep the ureter tube 1 in its position when withdrawing the mandrins 5, 8 from the ureter tube 1.

Figure 1B:
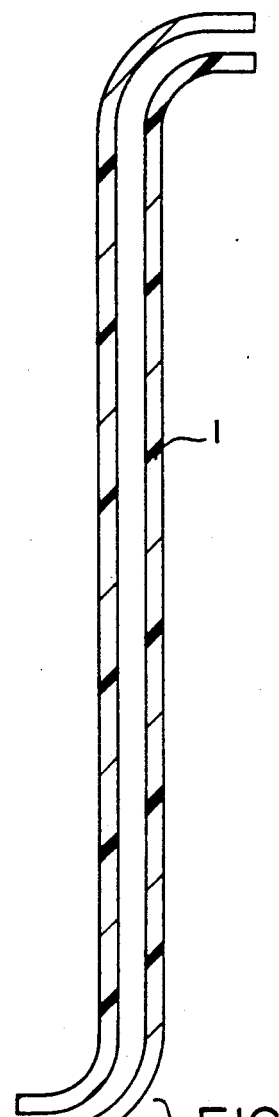
FIG. 1B shows a longitudinal cross-sectional view of the apparatus demonstrating the inherent curvature due to the "memory" of the ureter tube. The inner mandrin, outer mandrin and auxiliary tube are shown as withdrawn from the ureter tube.
Figure 1B:
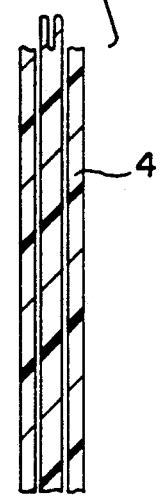

FIG. 1B shows the ureter tube 1 after the clamping 7 is released and the mandrins 5, 8 and the auxiliary tube 4 are withdrawn. The memory parts of the ureter tube are no longer straightened and reassume their original "pig-tail" form to this secure the introduced ureter tube 1 in the ureter and prevent undesired displacement.

In the embodiment according to FIG. 2, the above-mentioned drainage channel 3 is provided merely in the tip range of the ureter tube 1. In addition, mandrin shaft 5 in this embodiment terminates already somewhat above the enlargement 6 which is here in the form of a sleeve. In this fashion, upon removal of the mandrin inner shaft 8, the X-ray contrasting medium, as already explained, may flow into the lumen 15 up to the opening 14 and thence into the urethra. FIG. 2 shows the screw clamp 12 which is provided centrally of the mandrin and which releasably connects the mandrin with the auxiliary tube 4 Such a screw connection 12 has the advantage that it completely seals and simultaneously clamps the cylindrical, annular space between the auxiliary tube 4 and the mandrin outer shaft 5 while clamp 10 acting from the outside on the auxiliary tube 4 does not close the entire aforementioned annular space but only the portions of this annular space which are located in the clamping range.

Figure 3:
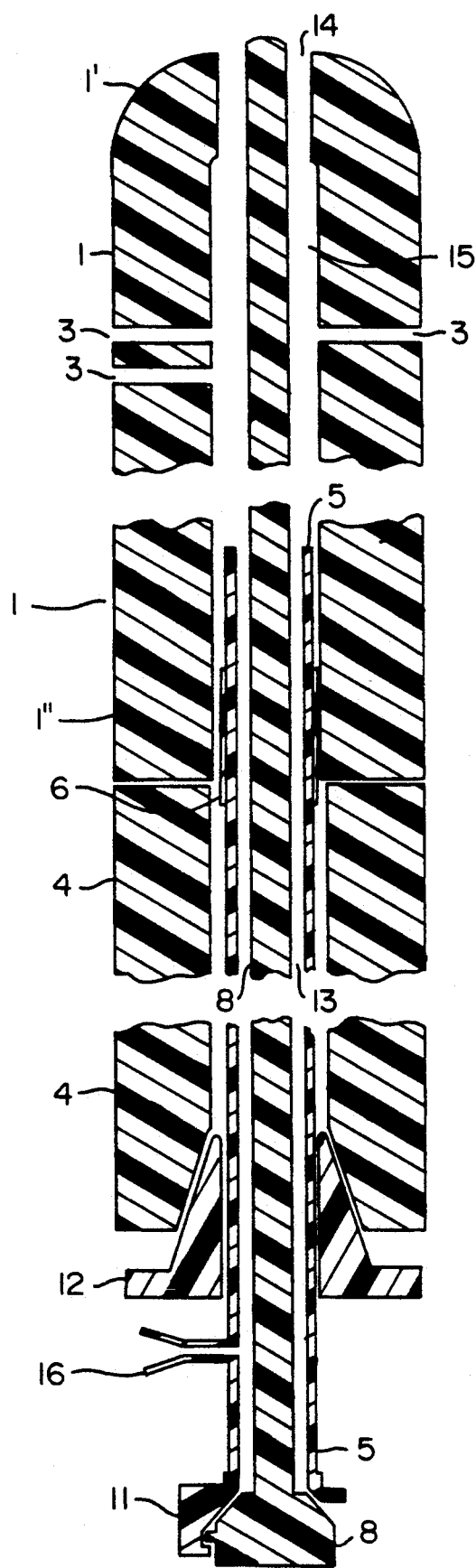
FIG. 3 is a third embodiment of the invention likewise in longitudinal section.

FIG. 3 shows an embodiment of the invention which in its general design corresponds to that of FIG. 2. However, the mandrin outer shaft 5 could also be extended up to the tip of the ureter tube 1 as represented in FIG. 1. The difference between the embodiment according to FIG. 3 with respect to the embodiments of FIGS. 1 and 2 consists in that in the subject matter of FIG. 3 the so-called lumen 13, that is the free annular-cylindrical space between mandrin inner shaft 8 and the mandrin outer shaft is larger, namely to the extent that upon introduction of the mandrin inner shaft 8 an X-ray contrasting medium may be injected from an injecting stud 16 to the opening 14 and therefore into the urethra or the renal pelvis outlet system. If the mandrin outer shaft 5 does not, as shown in FIG. 3, extend to the opening 14 but terminates somewhat below this opening, the further advantage of a yet larger lumen 15 in the upper range of the ureter tube ensues. This lumen enlargement for the surgeon in connection with the introduction of the X-ray contrasting medium, the withdrawal and reinsertion of the inner mandrin shaft 8.

Figure 4:
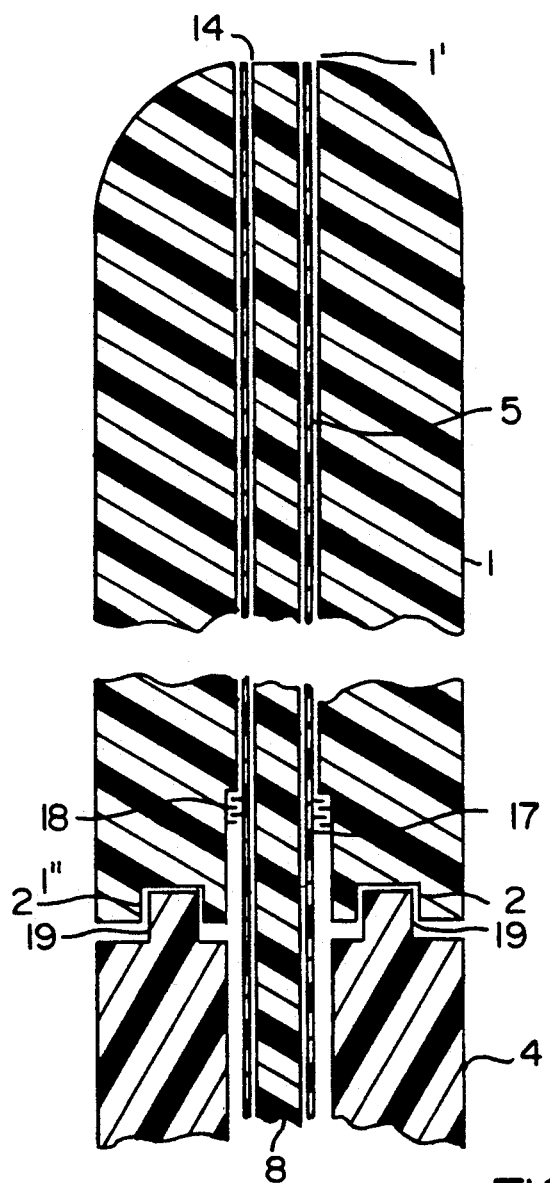
FIG. 4 is a fourth embodiment of the invention, also shown in longitudinal section and which is based on the subject of DE-OS 38 24 244.

FIG. 4 shows an embodiment of the invention with a releasable connection in the form of a screw connection 17,18. This is based on an arrangement according to DE-OS 38 24 244. Here numeral 17 denotes a thread portion on the mandrin outer shaft 5 and numeral 18 denotes a cooperating thread on the ureter tube 1, namely its end range 1" which adjoins the auxiliary tube. Projections 19 of the auxiliary tube 4 engage recesses 2 of the end 1" of the ureter tube 1.

Each of the described and illustrated features as well as their combinations with each other are of inventive significance.

What is claimed is:

1. An arrangement comprising a ureter tube having proximal and distal ends, a double mandrin having proximal and distal ends, inner and outer walls, and an outer mandrin and an inner mandrin which inner mandrin is longitudinally movable inside and relative to the outer mandrin, and an auxiliary tube having proximal and distal ends, the distal end of the auxiliary tube is in contact with the proximal end of the ureter tube, said ureter tube and auxiliary tube containing and being slidable over the outer mandrin, and said outer mandrin being releasably connected with said ureter tube by first releasable clamping means and said outer mandrin being releasably connected with said auxiliary tube by a separate second releasable clamping means, to form a functional unit of double mandrin, ureter tube and auxiliary tube, wherein both proximal end and the distal end of the ureter tube have openings and inherent curvatures and the distal end of the ureter tube has a central opening surrounded by the distal tip of the ureter tube, which distal tip has a distal face and wherein near the proximal end of the outer mandrin there are provided means for facilitating the introduction of an X-ray contrasting medium, and whereby said contrasting medium is enabled to flow through the length of said outer mandrin in a substantially rectilinear path via the open distal end of the outer mandrin and the central opening of the distal end of the ureter tube where it exits and arrangement.

2. An arrangement as claimed in claim 1, wherein the spacing between the inner mandrin and the outer mandrin provides a lumen sufficient for said contrasting medium to be introduced without the prior removal of the inner mandrin.

3. An arrangement as claimed in claim 2, wherein said facilitating means is in the form of a lateral connecting-piece for the introduction of the X-ray contrasting medium, said connecting-piece being provided at the proximal end of the outer mandrin extending from the proximal end of the auxiliary tube.

4. An arrangement as claimed in claim 1, wherein the distal end of the outer mandrin upon insertion is approximately in alignment with the distal ureter tube tip surrounding said central opening.

5. An arrangement as claimed in claim 1, wherein siad facilitating means is in the form of a connecting-piece for the attachment of a syringe serving for the introduction of the X-ray contrasting medium, said connecting-piece being provided at the proximal end of the outer mandrin extending from the proximal end of the auxiliary tube.

6. An arrangement as claimed in claim 1, wherein the first clamping means between the outer mandrin and the ureter tube is compressed of a material enlargement of a portion of the outside wall of the outer mandrin resulting in a strongly increased frictional force between said enlarged portions of the outer mandrin and a counter-surface of the inner wall of the ureter tube.

7. An arrangement as claimed in claim 1, wherein the first clamping means between the outer mandrin and the ureter tube is comprised of a material enlargement of a portion of the inner wall of the ureter tube resulting in a strongly increased frictional force between said enlarged portions inside of the ureter tube and an outer counter-surface of the outer mandrin.

8. An arrangement as claimed in claim 1, wherein the first clamping means between the outer mandrin and the ureter tube is comprised of an insert disposed between the outer mandrin and the ureter tube.

9. An arrangement as claimed in claim 1, wherein the second clamping means between the outer mandrin and the auxiliary tube is comprised a screw clamp.

10. An arrangement comprising a ureter tube having proximal and distal ends, the distal end containing a distal tip; a double mandrin having proximal and distal ends, an inner wall and an outer wall and an outer mandrin and an inner mandrin, which inner mandrin is longitudinally movable inside and relative to the outer mandrin, an auxiliary tube having proximal and distal ends, the distal end of the auxiliary tube being in contact with the proximal end of the ureter tube, said ureter tube and auxiliary tube containing and being slidable over the outer mandrin, and said outer mandrin being releasably connected with said ureter tube by first clamping means and said outer mandrin being releasably connected with said auxiliary tube by a separate second clamping means, to form a functional unit of double mandrin, ureter tube and auxiliary tube, and wherein both ends of the ureter tube have openings and inherent curvatures and the distal end of the ureter tube has a central opening surrounded by the distal tip of the ureter tube, which distal tip has a distal face, and wherein the distal ends of the outer mandrin and the inner mandrin are approximately in alignment with the distal outer surface of the distal ureter tip surrounding said central opening, whereby traumatization of the urethra during the introduction of the ureter tube with the outer mandrin and the inner mandrin is avoided.

11. An arrangement as claimed in claim 1, wherein the inner mandrin has a distal face, which distal face is domed outwardly and, when positioned approximately in alignment with the distal face of the distal ureter tube tip, continues the outwardly directed curvature of the distal face of the ureter tube tip surrounding said central opening.

12. An arrangement as claimed in claim 10, wherein the distal end of the inner mandrin projects from the distal end of the ureter tube tip.

13. An arrangement as claimed in claim 10, wherein the distal ends of the inner mandrin and of the outer mandrin project from the distal end of the ureter tube tip.

14. An arrangement as claimed in claim 10, wherein a releasable mandrin coupling is provided between a proximal portion of the outer mandrin and a proximal of the inner mandrin.

* * * * *

UNITED STATES PATENT AND TRADEMARK OFFICE
CERTIFICATE OF CORRECTION

PATENT NO. : 5,295,954
DATED : March 22, 1994
INVENTOR(S) : Hans-Ernst SACHSE

It is certified that error appears in the above-indentified patent and that said Letters Patent is hereby corrected as shown below:

In the Abstract, line 7, "pear" should be --near--.

Claim 1, column 7, line 32, "and" should be --said--.

Claim 6, column 7, line 59, "compressed" should be --comprised--.

Claim 11, column 8, line 43, "as claimed in claim 1" should be --as claimed in claim 10--.

Signed and Sealed this

Sixteenth Day of August, 1994

Attest:

BRUCE LEHMAN

Attesting Officer          Commissioner of Patents and Trademarks